United States Patent
Budig et al.

(10) Patent No.: US 7,875,761 B2
(45) Date of Patent: Jan. 25, 2011

(54) BEVELLED FOAM

(75) Inventors: Klaus Budig, Oelstykke (DK); Brian Nielsen, Goerloese (DK)

(73) Assignee: Coloplast A/S, Humlebaek (DK)

( * ) Notice: Subject to any disclaimer, the term of this patent is extended or adjusted under 35 U.S.C. 154(b) by 313 days.

(21) Appl. No.: 11/991,929

(22) PCT Filed: Sep. 26, 2006

(86) PCT No.: PCT/DK2006/000525

§ 371 (c)(1),
(2), (4) Date: Mar. 13, 2008

(87) PCT Pub. No.: WO2007/033679

PCT Pub. Date: Mar. 29, 2007

(65) Prior Publication Data

US 2009/0076431 A1    Mar. 19, 2009

(30) Foreign Application Priority Data

Sep. 26, 2005    (DK) ............................. 2005 01340

(51) Int. Cl.
*A61F 13/00*    (2006.01)
(52) U.S. Cl. .......................................... 602/42; 602/58
(58) Field of Classification Search ............. 602/41–54, 602/8
See application file for complete search history.

(56) References Cited

U.S. PATENT DOCUMENTS

| | | |
|---|---|---|
| 3,978,855 A | 9/1976 | McRae et al. |
| 3,990,440 A | 11/1976 | Gaylord, Jr. |
| 4,055,388 A | 10/1977 | Johns |
| 5,195,945 A * | 3/1993 | Sandvig et al. ................ 602/8 |
| 5,356,372 A | 10/1994 | Donovan et al. |
| 5,409,472 A * | 4/1995 | Rawlings et al. ............ 604/307 |
| 5,643,187 A | 7/1997 | Naestoft et al. |
| 5,792,089 A * | 8/1998 | Penrose et al. ................ 602/42 |
| 6,254,554 B1 | 7/2001 | Turtzo |
| 2002/0160682 A1* | 10/2002 | Zeng et al. ................... 442/411 |

FOREIGN PATENT DOCUMENTS

WO    WO 91/01706    2/1991

* cited by examiner

*Primary Examiner*—Michael A. Brown
(74) *Attorney, Agent, or Firm*—Coloplast Corp., Coloplast A/S; Daniel G. Chapik; Nicholas R. Bauman (57) ABSTRACT

The invention relates to a foam dressing with a bevelled edge and where the density at the edge is higher than the density at the central part of the foam. The high density at the edges causes gel blocking of the wound exudate thereby preventing leakage of exudate through the edges. In a preferred embodiment the foam dressing is non-adhesive. The foam dressing may have a water-impervious backing layer, which extends all the way over the top of the dressing and down to the wound-contacting surface. The wound dressing is particularly useful in treatment of venous ulcers in connection with compression bandages, as the bevelling of the edges markedly reduces the indentations in the leg following use of this dressing when compared to a dressing with straight edges.

17 Claims, 5 Drawing Sheets

BEVELLED FOAM

This is a national stage of International Application No. PCT/DK2006/000525 filed on Sep. 26, 2006 and published in English.

FIELD OF THE INVENTION

The present invention relates to a foam typically a foam as part of a wound dressing with bevelled parts and a process for manufacturing foam, e.g. polyurethane foam with bevelled parts.

BACKGROUND

Venous leg ulcers may have a high level of exudation. These wounds are often treated with a highly absorbing wound dressing such as foam dressing. Due to the underlying venous insufficiency the treatment is combined with compression therapy. The optimal dressing on these wounds should therefore be able to handle the exudation of the wound, but also be in compliance with the compression therapy.

Compression therapy is used to support the back flow of blood from the legs by applying an external pressure on the legs. When used in connection with treatment of a venous ulcer, this pressure also causes a pressure on the foam dressing and on the surrounding skin.

In general, foam dressings have a thickness of up to 6 mm. The pressure from the compression therapy on the foam dressing and the skin may lead to indentations on the skin. These indentations may be more or less pronounced depending on the degree of oedema in the leg and the dressing used. In severe cases, it has been observed that at the edge of the indentations, the skin deteriorates and a new ulcer is formed.

WO91/01706 provides a conformable wound dressing comprising an absorbent layer comprising polymeric foam, a wound facing discontinuous adhesive layer over one surface of said absorbent layer and a layer of a liquid impervious moisture vapour permeable material over the opposed surface of said absorbent layer wherein the thickness of the absorbent layer at two opposed margins is substantially less than the thickness of the absorbent layer between said margins.

The skin surrounding a venous leg ulcer may be extremely fragile. In order to avoid deterioration of this skin, adhesive foam dressings are not suitable for use.

Venous leg ulcers may, as earlier described, have high levels of exudation. As the non-adhesive foam dressing absorbs the wound exudate during the wear time, the absorption capacity of the foam may reach its maximum. When the maximum absorption capacity is reached, the absorbed wound exudate approaches the edge of the dressing. If the dressing is not changed in due time, the absorbed wound exudate may leak out from the edge portion of the non adhesive foam dressing to the ordinary stocking and/or the compression stocking causing discomfort for the user. In some cases, this may lead to maceration and creation of new venous leg ulcers, which is very undesirable.

Straight edges of the dressing may lead to indentations of the leg when the dressing is used in connection with a compression bandage.

Due to the reasons mentioned above, there is still a need for a non-adhesive foam dressing designed in such a manner, that the risk of leakage is minimised and the risk of skin deterioration caused by indentations from compression therapy is reduced or eliminated.

A high density at the edges would prevent leakage of wound exudate through the edge. However, this would further enhance the risk of indentations in the leg.

The present invention provides a solution to the above object by supplying non-adhesive foam dressing where the edge portion of the dressing comprises a bevelling with higher density than the central part of the dressing and a method of producing the bevelling.

By bevelling the edges and providing a higher density at the edges it is possibly to achieve a wound dressing which at the same time reduces the risk of leakage and indentations in the leg and where the wound dressing still has high absorption capacity.

The invention also provides a foam dressing having a bevelled edge with higher density than the central part of the dressing and where the backing layer extends all the way to the wound-contacting surface defined as the underside of the dressing designed to cover the wound, when the dressing is in use.

SUMMARY

The present invention relates to non-adhesive foam dressing with bevelled edges. The bevelled edge is carried out in such a manner that the density of the foam is increased in the bevelled edge portion compared to the central portion of the foam dressing. Such a dressing provides reduced indentations on the skin due to the bevelled edge. Furthermore, such dressing reduces the risk of leakage as the foam density on the edge portion is increased thereby the edge portion functions as a barrier for the wound exudate. This will prevent wound liquid being transported through the edge portion of the dressing and thereby avoiding leakage out of the edge portion of the dressing. This is illustrated in detail in example 2.

DETAILED DISCLOSURE

One aspect of the invention relates to a non-adhesive foam dressing wherein the density of the foam material is higher at the edge portion of the dressing than it is at the central portion of the dressing.

Figure 3:
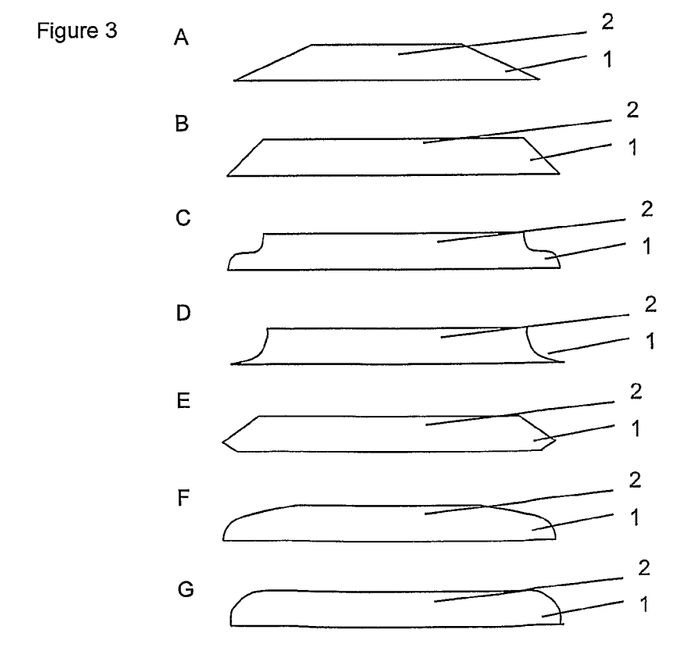
FIG. 3: Samples of edge-shapes of the wound dressing when it is bevelled according to the invention.

The edge portion of a bevelled foam dressing (1) is defined as the portion of the dressing where the foam has a reduced thickness compared to the central portion (2) of the foam (see FIG. 3).

The edge portion of a non-bevelled foam dressing is defined as the outmost 1 cm of the rim of the foam, such as the outmost 0.8 cm, the outmost 0.7 cm, the outmost 0.6 cm, the outmost 0.5 cm, the outmost 0.4 cm, or even the outmost 0.3 cm of the rim of the foam.

The fact that the dressing is non-adhesive provides direct contact between a wound-contacting surface of the foam dressing and the wound. This is desirable as slough and proteinous material from the wound is better absorbed into the dressing. This proteinous material often contains enzymes that can break down newly formed tissues explaining why optimal absorbance is needed. Wound contacting layers like nets, perforated films and adhesives may block absorption or serve as reservoir for wound fluid in contact with wound and/or surrounding skin, causing delay of wound healing.

Venous leg ulcers may have high exudate levels, explaining why it is desirable to have foam dressing with high absorption capacity even under compression. Typically, hydrophilic foam with high density tends to absorb more than less dense foam. However, if the foam has a too high density there might be a tendency of gel blocking causing only limited wound fluid absorption and transportation. In addition, the denser a foam, the less compressible it is. Therefore, the density of hydrophilic foam in the central portion is designed in such a manner that the absorption capacity is optimised but also so that no gel blocking occurs and indentations are minimised. In one embodiment, the non-adhesive foam dressing has a density of between 100 and 400 kg/m$^3$ such as between 120 and 300 kg/m$^3$, or between 130 and 250 kg/m$^3$ or even between 140 and 225 kg/m$^3$. In a particular preferred embodiment of the invention, the density is between 150 and 200 kg/m$^3$.

Measuring density is common practice. Here, density should be measured under conditions of typical use that is at a temperature of 20° C., air pressure of 1013 hPa and relative humidity of 40%. Under these conditions, a sample of the foam material is measured to determine the volume V and weighed to determine the mass m and the density d calculated as d=m/V. Unless otherwise mentioned, the density of the edge portion is considered to be the average density over the entire edge portion.

It is central to the present invention that the edge portion of the dressing has a higher density than the central portion of the dressing. The problem of pressure on the surrounding skin is especially pronounced when used under a compression bandage, typically for venous ulcers. As the foam according to the invention will tend to cause a barrier effect of the edge portion of the dressing, the tendency to leak is markedly reduced. Example 2 illustrates this reduced tendency to leak in more detail. In one embodiment of the invention, the density of the foam material at the edge portion is at least 50% higher than the density of the foam material at the central portion of the foam dressing such as 75% higher or double density even up to five times higher.

In another embodiment of the invention the increase in density is of a factor of 2 to 12 either linearly or non-linearly when the density is measured through-out the edge portion.

The edge portion could be defined by different zones, where the first zone is defined by the outermost 2 mm's of the edge portion, the second zone extends from 2-4 mm's into the dressing and the third zone extends from 4-6 mm's into the dressing from the edge.

In one embodiment the average density of the first zone is at least two times the average density of the second zone.

In a further embodiment the average density of the first zone is at least three times the average density of the third zone. In a still further embodiment the average density of the first zone is at least three times the density of the central portion of the dressing while at the same time the average density of the entire edge portion is up to two times the density of the central portion of the dressing.

In another embodiment the average density of the foam material of the entire edge portion is at least 500 kg/m$^3$. In a further embodiment the density of the foam material of the central portion is between 150 kg/m$^3$ and 200 kg/m$^3$ while the average density of the edge portion is between 250 kg/m$^3$ and 450 kg/m$^3$ and in a still further embodiment the average density of the first zone of the dressing is between 600 kg/m$^3$ and 900 kg/m$^3$.

Another aspect of the invention relates to a foam dressing having an edge portion and a central portion, where the density of the foam material is higher at the edge portion of the dressing than it is at the central portion of the dressing, and further comprising a backing layer extending all the way over the top of the dressing and completely covering the exterior side of the edge portion of the foam dressing, thereby further reducing the risk of leakage at the edges of the dressing.

The backing layer may be of any suitable material known per se for use in the preparation of wound dressings e.g. a foam, a nonwoven or a polyurethane, polyethylene, polyester or polyamide film.

A suitable material for use as a backing layer is a polyurethane film. A preferred low friction film material is disclosed in U.S. Pat. No. 5,643,187.

The wound dressing according to the invention may comprise one or more active ingredients, e.g. a pharmaceutical medicament. This opens for a combined medical treatment of a wound, where the dressing absorbs wound exudate and the pharmaceutical medicaments will be applied to the wound. The pharmaceutical medicaments can e.g. be incorporated in the wound dressing or may be provided as a separate layer or coating on the wound dressing.

Examples of such pharmaceutical medicaments includes a cytochine such as a growth hormone or a polypeptide growth factor such as TGF, FGF, PDGF, EGF, IGF-1, IGF-2, colony stimulating factor, transforming growth factor, nerve stimulating growth factor and the like giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorohexidine, silver salts such as sodium silver zirconium phosphate (available as Alphasan), sulphadiazine, silver nitrate, silver acetate, silver lactate, silver sulphate, silver sodium thiosulphate or silver chloride, zinc or salts thereof, metronidazol, sulpha drugs, and penicillin's, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as NSAIDs (e.g. Ibuprofen), lidocaine or chinchocaine, emollients, retinoids or agents having a cooling effect which is also considered an aspect of the invention.

The active ingredient may also comprise odour controlling or odour reducing material.

The present invention provides a bevelled foam product without a hard rubber-like edge. This avoids the sharp edges (that can cut the skin) during compression. As the product according to the invention does not have either an adhesive layer or a net between the foam and the skin, there is nothing to protect the skin from such rubber-like edges. Thus, this is the first product suitable for compression bandage. This is illustrated in more detail in example 3.

The present invention can be carried out with various types of foam material. The types of foam material and their manufacture are known to the skilled person. Preferred foamed materials are hydrophilic polyether based polyurethane.

There are different ways to increase the density of the edge portion of the foam dressing. In one embodiment this is done, as described below in causing the edge portion of the dressing to be a bevelled edge portion.

One suitable way of increasing the density of the foam material in the edge portion and at the same time obtaining a bevelled edge portion, is to contour the foam material during the foaming process, this is to be done prior to end-of-cure.

During such contouring process, the edge portion is compressed providing the higher density at the edge portion compared to the central portion of the foam.

The foam may also be casted directly onto the backing layer. In a typical scenario the uncured foam mixture is poured out on a PU-film in contact with a conveyer belt. The uncured foam mixture is encapsulated between the PU-film and a supportive film. The foam is allowed to rise and cure. However, before the foam mixture reaches the cured state, the foam is contoured into multiple discrete foam pads. The contouring of the material may be done in different manners, for example by kiss-cutting rolls. Kiss-cutting may be performed from one or both sides of the foam sheets, where the rolls have contoured shapes in order to introduce embossed shapes of the foam when the foam passes the kiss cutting rolls. If only one of the kiss-cutting rolls has a contoured shape, the contoured roll may be both the upper and the lower roll.

Figure 1:
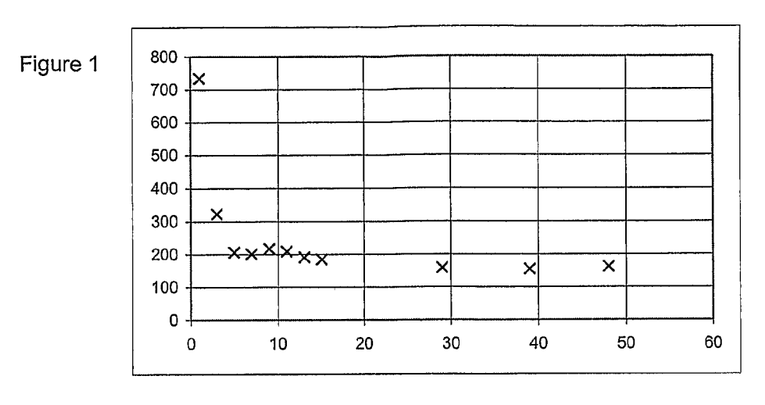
FIG. 1: An example of a density-profile of the wound dressing according to the invention.

FIG. 1

This figure shows the density profile of a foam dressing according to the invention. The densities were measured in different points reaching from the edge of the foam to the middle of the foam. The measuring of the densities was done according to the method described in example 1.

The figure shows the density in $kg/m^3$ as a function of the distance to the edge in mm. The distance to the edge is defined as the distance from the middle of the cut pieces to the edge.

Figure 2:
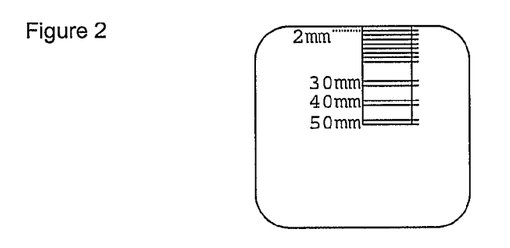
FIG. 2: The layout for cutting test pieces used to determine the density profile.

FIG. 2

FIG. 2 shows the cutting layout of the foam dressing used to make the density profiles shown in FIG. 1 and example 1.

FIG. 3

This figure illustrates samples of edge-shapes when bevelled according to the invention. The central part of the foam dressing (2) has a lower density than the edge part (1). A and B show examples of trapezoidal shapes of the dressing that is, the bevelling is linear. C shows a curved bevelling which is concave in one part and convex in another part of the curve. The first part of the curve extending from the wound-contacting surface to the middle of the edge portion is convex. The second part extending from the middle of the edge portion to the top is concave. D shows a concave bevelling which is quite thin near the skin-contacting surface of the dressing. E shows a bevelling with two straight edges at an angle to each other, which leaves pointed edges of the dressing. F and G show two convex shapes of the bevelling extending different distances into the dressing, i.e. the width of the edge portion differs.

All of the above embodiments except E has a substantially planar wound-contacting surface.

FIGS. 4-8

FIGS. 4-8 show the test set-up used for testing the gel-blocking effect of the bevelled edges with high density (approx. 600 $kg/m^3$) compared to cut edges with the same density (approx. 200 $kg/m^3$) as the central part of the pad.

Figure 4:
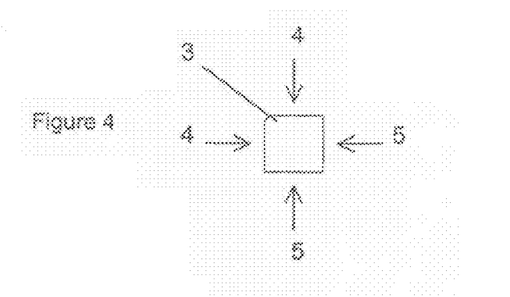
FIGS. 4-8: Test set-up used for testing gel-blocking effect of the wound dressing.

The foam dressing to be tested is shown in FIG. 4. The test is performed on pieces of 40×40 mm squares (3), cut in such a way that two sides have bevelled edges (4), while the other two sides have straight edges (5) obtained by cutting the edges.

Figure 5:
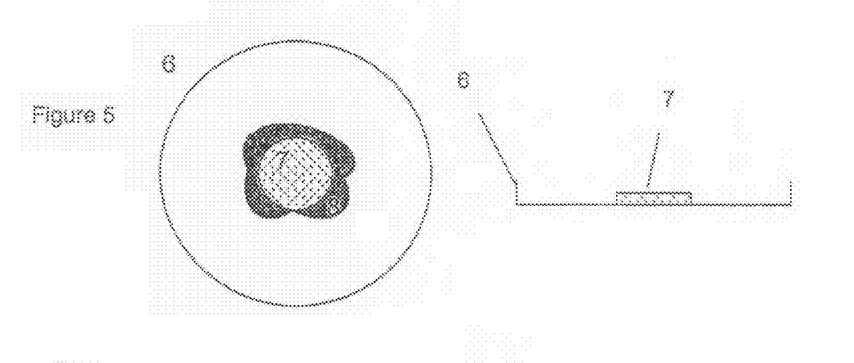

FIG. 5 shows top view and a side view of the part of the set-up illustrating a wound. A micro porous plate (7) soaked in a synthetic wound exudate composition (8) is placed in a lid to a petri dish (6). This is used to illustrate a heavy exudating wound.

Figure 6:
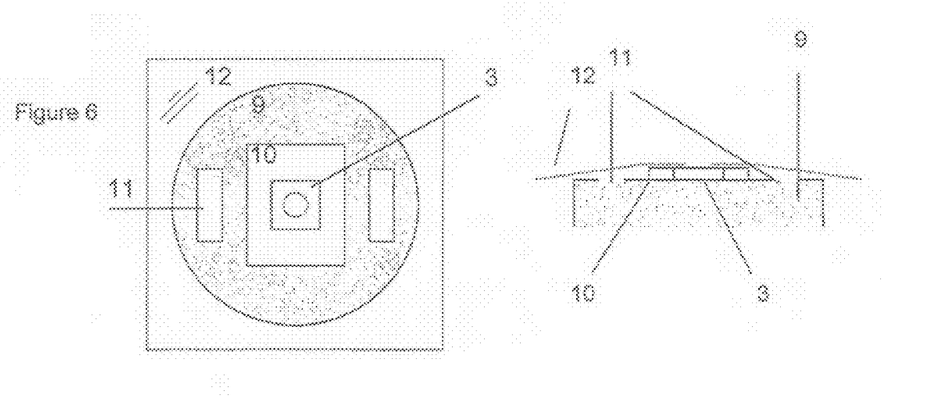

FIG. 6 shows top view and side view of the part of the set-up when holding the foam dressing. A foam frame (10) is placed on the bottom of a petri dish (9). The central part of the foam frame corresponding to the test size of the dressing (3) is removed. The dressing to be tested (3) is placed inside the foam frame. As the dressing (3) soaks up the synthetic wound exudate, it is possible to measure the leaking from the edges of the dressing in the foam frame (10). A plastic film (12) is placed on top and fastened to the bottom of the petri dish (9) using double-adhesive tape (11). The plastic film (12) has a hole at the middle, which is placed over the dressing. The plastic film (12) is used to ensure that the dressing and not the foam frame soaks up the exudate.

Figure 7:
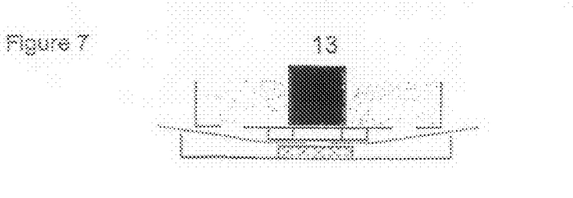

FIG. 7 shows a side view of the set-up in assembled position. The petri dish (9) is placed bottom-down inside the lid (6). A weight (13) is placed inside the petri dish to exert the necessary pressure on the dressing, which corresponds to the pressure exerted by a regular compression bandage.

Figure 8:
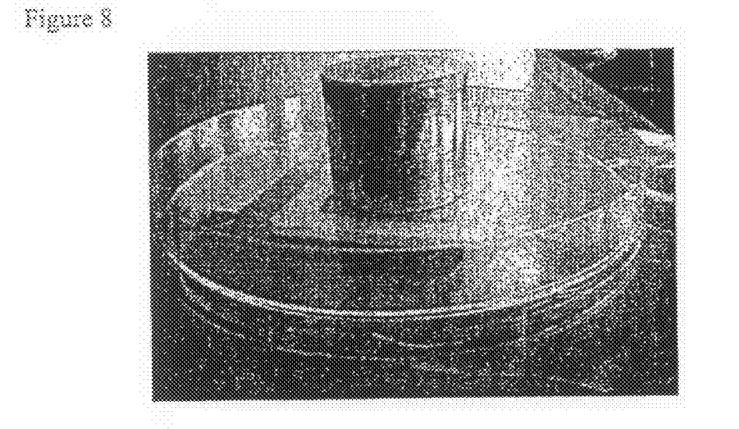

FIG. 8 shows a photo of the set-up.

Figure 9:
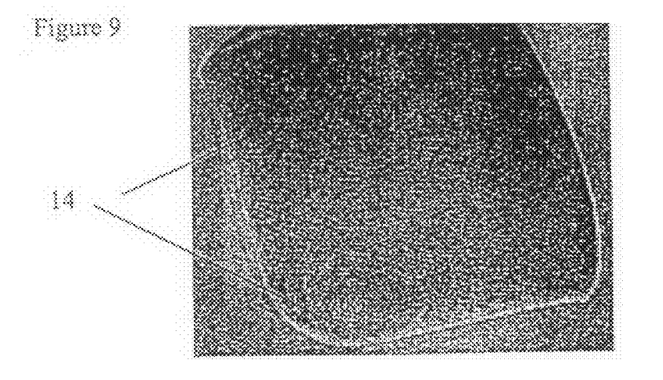
FIGS. 9-10: Photos further illustrating the gel-blocking effect.
Figure 10:
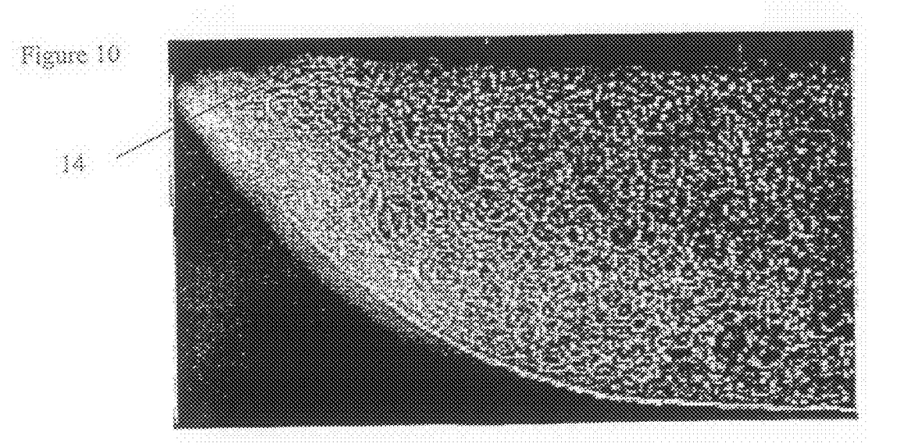

FIGS. 9-10

FIGS. 9-10 illustrate the liquid barrier in photos of foam dressing according to the invention that is saturated in synthetic exudates. The figures show a top view and a cross section respectively of a foam dressing saturated with red synthetic wound exudate.

The photos clearly illustrates that the liquid stops at the high-density edges, as the edges (14) are not coloured by the synthetic exudate. Contrary to this, the synthetic exudate reaches the border at the bottom of photo. This shows that wound exudate would not leak from the dressing through the edges.

Figure 11:
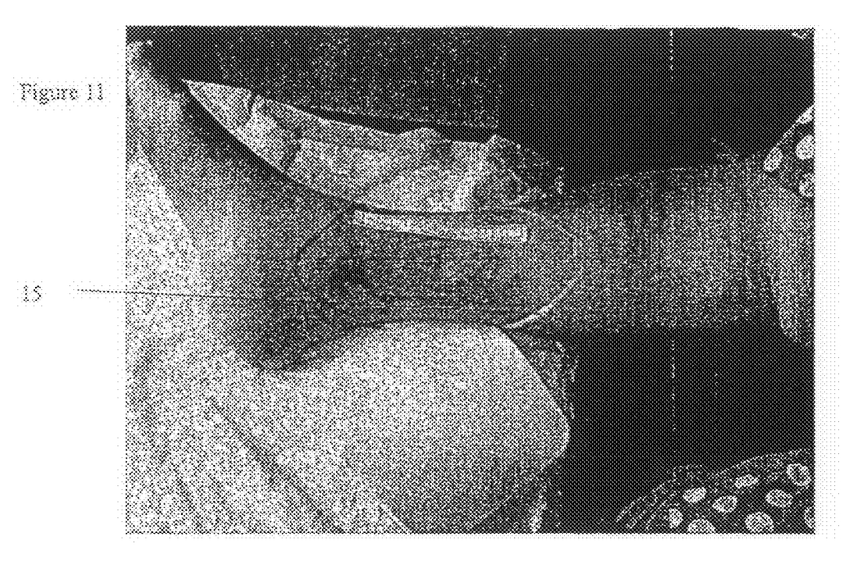
FIGS. 11-12: Photos of indentation in a leg caused by a conventional foam dressing and caused by foam dressing according to the invention.
Figure 12:
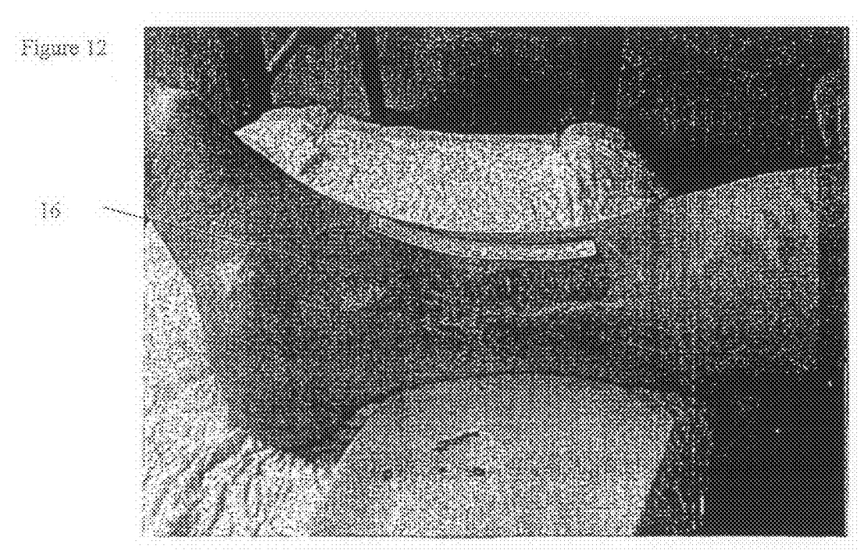

FIGS. 11-12

FIGS. 11-12 show photos of a leg of the same patient having a venous leg ulcer. FIG. 11 shows the leg after it was bandaged with conventional foam dressing without bevelled edges and FIG. 12 shows the same leg after being bandaged with a foam dressing according to the invention.

Figure 13:
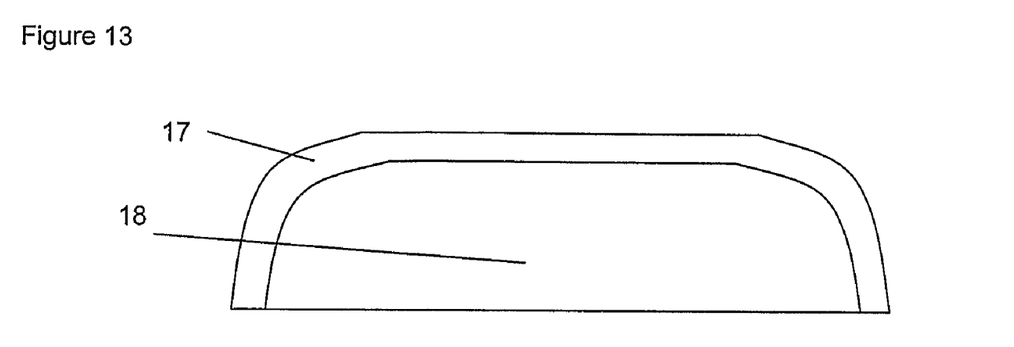
FIG. 13: Cross-section of the dressing showing the backing layer extending to the wound-contacting surface.

FIG. 13

The figure shows a cross-section of the backing layer (17) and the foam core (18), the thickness of the backing layer is largely distorted compared to the real foam dressing. The figure illustrates that the backing layer (17) extends all the way to the wound-contacting surface. As the backing layer is water impervious it would help to reduce leakage at the edges even further.

REFERENCE LIST (1) Bevelled edges of foam dressing
(2) Central part of foam dressing
(3) Dressing to be tested, test piece cut as a square 40 mm×40 mm cut so as to leave two edges bevelled and two edges cut
(4) Bevelled edges of the test piece
(5) Cut edges of the test piece
(6) Lid to Petri dish ø140 mm
(7) Micro porous plate, Schott Duran, ø60 mm
(8) Synthetic wound exudates containing water, tri-sodium citrate dihydrate, and Allura Red (food dye).
(9) Petri dish ø140 mm
(10) Foam frame, 60×60 mm Biatain with paper. Central square of 40×40 mm removed.
(11) Double sided tape, 3M.
(12) Plastic film, waterproof, with a round hole ø25 mm.
(13) Weight, Alu. When pressing against a ø60 mm plate, it corresponds to a pressure of 40 mm Hg.
(14) Liquid barrier at the bevelled edges of the foam dressing
(15) Indentations at leg using a conventional foam dressing without bevelled edges
(16) Indentation at leg using a foam dressing according to the invention
(17) Backing layer
(18) Foam core

Example 1

Density Measurements

The density of 3 specimens was measured. The foam dressing was cut, as it appears from FIG. 2. The test pieces were punched out. The length, width and thickness of the test pieces were measured, and subsequently the pieces were weighed. The densities were calculated as mass divided by volume. All of the test pieces were 2 mm in the length direction and 20 mm wide. Table 1 shows the origin of the pieces as the distance into the dressing, the thickness, the weight and the density. Comparable to that, table 2 shows the values of specimen no. 2 and table 3 shows the values of specimen no. 3.

TABLE 1

Density measurements on specimen 1.

| Origin of test piece (mm) | Thickness (mm) | weight (g) | Density (kg/m$^3$) |
|---|---|---|---|
| 0-2 | 1.5 | 0.0350 | 583 |
| 2-4 | 3.0 | 0.0346 | 288 |
| 4-6 | 3.4 | 0.0327 | 240 |
| 6-8 | 3.5 | 0.0286 | 204 |
| 8-10 | 3.5 | 0.0291 | 208 |
| 10-12 | 3.5 | 0.0310 | 221 |
| 12-14 | 3.5 | 0.0351 | 251 |
| 14-16 | 3.5 | 0.0320 | 229 |
| 16-18 | 3.5 | 0.0290 | 207 |
| 18-20 | 3.5 | 0.0298 | 213 |
| 28-30 | 3.5 | 0.0284 | 203 |
| 39-41 | 3.5 | 0.0293 | 209 |
| 49-51 | 3.5 | 0.0292 | 209 |

TABLE 2

Density measurements on specimen 2.

| Origin of test piece (mm) | Thickness (mm) | weight (g) | Density (kg/m$^3$) |
|---|---|---|---|
| 0-2 | 1.2 | 0.0352 | 733 |
| 2-4 | 2.5 | 0.0322 | 322 |
| 4-6 | 3.4 | 0.0280 | 206 |
| 6-8 | 3.5 | 0.0281 | 201 |
| 8-10 | 3.5 | 0.0303 | 216 |
| 10-12 | 3.8 | 0.0317 | 209 |
| 12-14 | 3.8 | 0.0290 | 191 |
| 14-16 | 3.7 | 0.0272 | 184 |
| 29-31 NB! only 13.5 mm wide | 4.3 | 0.0183 | 158 |
| 39-41 | 4.3 | 0.0265 | 154 |
| 48-50 | 4.3 | 0.0278 | 162 |

TABLE 3

Density measurements on specimen 3.

| Origin of test piece (mm) | Thickness (mm) | weight (g) | Density (kg/m$^3$) |
|---|---|---|---|
| 0-2 | 1.8 | 0.0262 | 364 |
| 2-4 | 2.5 | 0.0263 | 263 |
| 4-6 | 2.8 | 0.0259 | 231 |
| 6-8 | 2.8 | 0.0269 | 240 |
| 8-10 | 3.0 | 0.0276 | 230 |
| 10-12 | 3.2 | 0.0262 | 205 |
| 12-14 | 3.2 | 0.0284 | 222 |
| 14-16 | 3.2 | 0.0309 | 241 |
| 16-18 | 3.4 | 0.0297 | 218 |
| 18-20 | 3.4 | 0.0280 | 206 |
| 39-41 | 3.8 | 0.0324 | 213 |
| 49-51 | 4.0 | 0.0309 | 193 |

The densities measured on specimen 2 were used as basis for the graph shown in FIG. 1. The foam dressing used in example 2 had a density profile as measured on specimen 1. The results show that the average density of the outermost 2 mm's is at least two times the density of the edge portion extending from 2-4 mm's into the dressing and for one of the specimens at least 3 times the density of the edge portion extending from 4-6 mm's into the dressing.

Example 2

Test of Leakage

This example illustrates the barrier effect obtained by the increased density at the edges of the bandage.

The experiments were performed with foam dressings saturated with liquid under a pressure similar to the pressure normally used with compression dressing.

Set-Up

A micro porous plate (7) was mounted inside a lid of a petri dish (6). 20 ml synthetic wound exudate composition (8) was added to the lid (6). The synthetic wound exudate composition (8), which was used for these experiments, consists of water, tri-sodium citrate dihydrate, and Allura Red (food dye).

At the outer side of a corresponding petri dish (9) the test piece (3) was surrounded by a foam frame (10) and mounted under plastic film (12), held by two pieces of double sided tape (11), so the hole in the film was placed towards the centre of the dressing. As explained earlier the test piece had two bevelled edges (4) and two straight edges (5) thereby making it possible to test the difference in leaking between the bevelled edges and the straight edges using only one test piece. The foam dressing was shaped as shown in FIG. 3G before it was cut.

Procedure

At 0 sec. the petri dish (9) was placed in the lid (6), so the test piece (3) was soaking synthetic exudate (8) from the porous plate (7) through the hole in the film (12). A weight (13) was applied which corresponds to 40 mm Hg according to the standard compression on venous leg ulcers.

After 35 seconds, the migration of the synthetic exudate into the foam frame was measured at the middle of all 4 foam sides by using a ruler.

Results

The described experiment was made 10 times, and the resulting migration into the foam frame appears from table 3. In the table Cut 1 and Cut 2 correspond to edges (5) in FIG. 4 while BE 1 and BE 2 correspond to edges (4).

TABLE 4

Results from the experiments

| Test no. | Cut 1 (mm) | Cut 2 (mm) | BE 1 (mm) | BE 2 (mm) |
|---|---|---|---|---|
| 1 | 4 | 4 | 0 | 0 |
| 2 | 2 | 2 | 0 | 0 |
| 3 | 2 | 3 | 0 | 0 |
| 4 | 1 | 1 | 0 | 0 |
| 5 | 1 | 2 | 0 | 1 |
| 6 | 3 | 2 | 0 | 0 |
| 7 | 3 | 3 | 0 | 1 |
| 8 | 2 | 2 | 0 | 0 |
| 9 | 3 | 3 | 0 | 0 |
| 10 | 3 | 4 | 1 | 1 |
| Average | 2.4 | 2.6 | 0.1 | 0.3 |

The results show that the bevelled edges function as barriers to leakage and thereby significantly prevent exudate to leak into the foam frame, while the exudate were able to leak from the two cut sides to be absorbed in the foam frame.

The results that show a small amount of leakage (test 5, 7 and 10) from the bevelled edges may be explained in that the foam edges were lifted a little and the leak then occurred in the foam next to the edges. This situation will not occur in real life, where a compression dressing will press the edges to the skin. The same argument cannot be used to the cut sides. Here the foam is directly in contact with the compression dressing.

Example 3

Test of Indentations

The test was performed on a patient having a venous ulcer. The experiment was conducted such that the leg of the patient was bandaged using a foam dressing in connection with a compression bandage. The bandage was left for 2 days. Following removal of the bandage a photograph was taken. Experiment 1 was done using a conventional foam dressing with straight edges and experiment 2 was done using a foam dressing with bevelled edges according to the invention. The bevelling was shaped as shown in FIG. 3G. The results appear in FIGS. 11-12 showing the indentations as a result of a conventional dressing (15) and as a result of a dressing according to the invention (16). The indentations in the leg in FIG. 12 (16) are much less pronounced than the indentations shown in FIG. 11 (15). This shows that using the foam dressing according to the invention helps preventing the deterioration of the fragile skin surrounding a venous ulcer.

The invention claimed is:

1. Non-adhesive foam dressing having an edge portion and a central portion, where the density of the foam material is higher at the edge portion of the dressing than it is at the central portion of the dressing and wherein the central portion of the foam dressing has a density of more than 100 kg/m$^3$.

2. Non-adhesive foam dressing according to claim 1, wherein the central portion of the foam dressing has a density of less than 400 kg/m$^3$.

3. Non-adhesive foam dressing according to claim 1, wherein an increase in the density of the edge portion is of factor of between 2 to 12 linearly or non-linearly when measured through-out the edge portion of the dressing.

4. Non-adhesive foam dressing according to claim 1, wherein the average density of a first zone defined by the outermost 2 mm's of the edge portion of the dressing is at least two times the average density of a second zone extending from 2-4 mm's into the edge portion of the dressing.

5. Non-adhesive foam dressing according to claim 1, wherein the average density of a first zone defined by the outermost 2 mm's of the dressing is at least three times the average density of a third zone extending from 4-6 mm's into the edge portion of the dressing.

6. Non-adhesive foam dressing according to claim 1, wherein the average density of a first zone defined by the outermost 2 mm's of the edge portion of the dressing is at least three times the density of the central portion of the dressing and where the average density of the entire edge portion is up to two times the density of the central portion of the dressing.

7. Non-adhesive foam dressing according to claim 1, wherein the average density of the foam material of the entire edge portion is at least 500 kg/m$^3$.

8. Non-adhesive foam dressing according to claim 1, wherein the density of the foam material of the edge portion at least is 50% higher than the density of the foam material of the central portion of the dressing.

9. Non-adhesive foam dressing according to claim 1, wherein the density of the foam material of the edge portion is at least 75% higher than the density of the foam material of the central portion of the dressing.

10. Non-adhesive foam dressing according to claim 1, wherein the density of the foam material of the edge portion is at least two times the density of the foam material of the central portion of the dressing.

11. Non-adhesive foam dressing according to claim 1, wherein the density of the foam material of the edge portion is up to 5 times higher than the density of the foam material of the central portion of the dressing.

12. Non-adhesive foam dressing according to claim 1, wherein the density of the foam material of the central portion is between 150 kg/m$^3$ and 200 kg/m$^3$ and the average density of the edge portion is between 250 kg/m$^3$ and 450 kg/m$^3$.

13. Non-adhesive foam dressing according to claim 1, wherein the average density of a first zone defined by the outermost 2 mm's of the dressing is between 600 kg/m$^3$ and 900 kg/m$^3$ and the density of the foam material of the central portion is between 150 kg/m$^3$ and 200 kg/m$^3$.

14. Non-adhesive foam dressing according to claim 1, wherein the edge portion is a bevelled edge portion.

15. Non-adhesive foam dressing according to claim 1, wherein the foam material is made of polyurethane foam.

16. Foam dressing having an edge portion and a central portion, where the density of the foam material is higher at the edge portion of the dressing than it is at the central portion of the dressing and further comprising a backing layer extending all the way over the top of the dressing and completely covering an exterior side of the edge portion of the foam dressing.

17. Foam dressing according to claim 16 where the foam dressing is non-adhesive.

* * * * *